United States Patent [19]
Holfert et al.

[11] Patent Number: 5,324,464
[45] Date of Patent: Jun. 28, 1994

[54] METHOD OF MAKING A BLOOD PUMPING MEMBRANCE FOR ARTIFICIAL VENTRICLES

[75] Inventors: John W. Holfert, Bountiful; Jeffery T. Juretich, Salt Lake City; Pamela A. Dew, Sandy, all of Utah

[73] Assignee: University of Utah Research Foundation, Salt Lake City, Utah

[21] Appl. No.: 880,084

[22] Filed: May 5, 1992

[51] Int. Cl.⁵ ............................................. B29C 41/14
[52] U.S. Cl. ................................. 264/130; 264/301; 264/305; 156/293; 623/3; 427/230
[58] Field of Search ................... 264/130, 301, 305; 623/3; 156/293; 427/230, 235

[56] References Cited

U.S. PATENT DOCUMENTS

| | | | |
|---|---|---|---|
| 3,978,187 | 8/1976 | Fletcher et al. | 264/305 |
| 4,222,127 | 9/1980 | Donachy et al. | 623/3 |
| 4,668,459 | 5/1987 | Joh | 264/305 |
| 4,781,715 | 11/1988 | Wurzel | 623/3 |
| 4,863,461 | 9/1989 | Jarvik | 623/3 |
| 4,976,729 | 12/1990 | Holfert . | |
| 4,981,484 | 1/1991 | Holfert . | |
| 5,089,020 | 2/1992 | Koppert . | |
| 5,392,879 | 3/1992 | Jarvik | 623/3 |

Primary Examiner—Catherine Timm
Attorney, Agent, or Firm—Thorpe, North & Western

[57] ABSTRACT

A method for fabricating a flexible, blood pumping membrane for use within an artificial ventricle, involves the steps of selecting a mold configured to provide a dome shaped diaphragm biased in a static mode to a systolic configuration and suitable for use within a ventricular housing as a part of a blood pumping membrane. The specific steps include forming the dome shaped diaphragm on a surface of the mold to include (i) a perimeter comprising at least a portion of a diaphragm/housing interface which is configured to connect the dome shaped diaphragm with the ventricular housing to enclose a blood pumping chamber, and (ii) an intermediate annular section of the dome shaped diaphragm extending inward from the diaphragm/housing interface in a configuration corresponding to that portion of the diaphragm when the ventricle is substantially at full systole.

9 Claims, 2 Drawing Sheets

METHOD OF MAKING A BLOOD PUMPING MEMBRANCE FOR ARTIFICIAL VENTRICLES

BACKGROUND OF THE INVENTION

1. 1. Field of the Invention

This invention pertains to a blood contacting membrane which operates as part of a pumping mechanism for displacement of blood through an artificial ventricle. More particularly, the present invention relates to a single layer, pumping membrane wherein one side of the pumping membrane constitutes the blood contacting diaphragm surface within the blood chamber of the ventricle.

2. Prior Art

Despite the growing need for an effective artificial ventricle to replace damaged heart organs, a commercially acceptable artificial ventricle remains a subject of considerable research and development, rather than commercial production. Certainly, many various ventricle designs have been offered for patient use; however, the state of the art continues to be primarily exploratory.

Numerous obstacles remain with respect to achievement of an artificial ventricle which can take its place in the medical community as a standard commodity. One such obstacle is the high cost of such devices, often placing them beyond the reach of day to day economic reality. This high cost arises because of the difficulty in manufacturing an acceptable pumping diaphragm which has minimal stress as it displaces between extended positions at systole and diastole. This stress occurs at folding sections of the diaphragm as it moves from full blood chamber expansion at diastole, through intermediate folds and deformation, to full inverse extension in systole. If these folds and deformations become localized at specific areas of the diaphragm, such areas may weaken as the localized deformations continue for millions of repetitions.

Numerous designs have been attempted which generate broad folding patterns which will avoid localized stress. U.S. Pat. No. 4,974,729 teaches the advantages of using elliptical pumping and blood diaphragms to develop more favorable folding patterns. U.S. Pat. No. 4,981,484, by the same inventor, further developed the elliptical diaphragm with a unique modification to curvature by flattening sections of the diaphragm to program a large fold pattern. Each of these designs utilized multiple membranes for forming the pumping diaphragm, because such a thin membrane minimizes the stress arising as it goes through its deformation.

More importantly, these membranes were molded with a downward curvature, corresponding to the shape of the diaphragm at diastole. This technique and diastole pattern has been virtually universal with respect to membranes formed within a rigid ventricular housing wherein the membrane displaces into a pumping chamber in concave form and extends upward into the blood chamber in convex configuration.

Because the membranes are molded in the downward or diastolic configuration, the perimeter is typically formed with an inverted U-shaped edge, with the outside leg of the U being the point of attachment to the outer housing. In this diastole configuration the membrane has no stress arising, because its molded shape is in original form as originally molded. Upon deformation of the diaphragm upward toward systole, the polymer shape is modified and the natural resilience of the elastomer will tend to increase the stress load to return the membrane to its original, downward configuration. This repeated occurrence of stress within the membrane tends to weaken the polymer at the points of local stress, and will eventually result in diaphragm failure.

This traditional pattern of forming the pumping diaphragm in a downward or diastolic configuration was also adopted in U.S. Pat. No. 4,089,020. This invention disclosure shows a monoseptal, biventricular design wherein the separating wall between the ventricles serves as a rigid support to opposing pumping diaphragms. As is noted in FIG. 7, both diaphragms are biased to a collapsed configuration against the rigid wall in the diastolic position, and must be inflated to realize the systolic mode.

Accordingly, a major problem persists with respect to management of elastic stress associated with diaphragm displacement during the repeated pumping cycle of the artificial ventricle. The existence of this stress required the use of multiple diaphragms in larger ventricles to maintain a sufficiently thin dimension so that elastic stress was minimized. Manufacture of such membranes required repeated dip molding, taking many days to complete fabrication. The total process resulted in extreme high cost in the production of an acceptable membrane for use as a human prosthetic. This high membrane cost contributed to a cost of an artificial heart reaching in the hundreds of thousands of dollars.

OBJECTS AND SUMMARY OF THE INVENTION

It is an object of the present invention to provide a blood contacting membrane which experiences reduced elastic stress within an artificial ventricle during pumping operations.

It is a further object of this invention to provide a blood contacting membrane that can serve as a pumping membrane as well, forming a single diaphragm between the pumping and blood chambers of an adult artificial ventricle.

It is yet another object to provide a blood contacting membrane which can be quickly and inexpensively manufactured, yet provide the reliability and performance equivalent to traditional membranes of much higher cost.

These and other objects are realized in an artificial ventricle comprising a ventricular housing including a blood pumping chamber with inlet and outlet ports and a pumping chamber including means for delivery of pumping fluid respectively to the chamber during systole and from said fluid during diastole. The ventricle includes a blood contacting membrane responsive to displacement by the pumping fluid between systole and diastole positions, said membrane being biased to a natural position corresponding to systole in the absence of any pumping force.

The invention also embodies a method for fabricating a flexible, blood pumping membrane for use within a ventricle, comprising the steps of:

a) selecting a mold configured to provide a dome shaped diaphragm suitable for use within a ventricular housing as part of a blood pumping membrane;

b) forming on the surface of the mold.

(i) the dome shaped diaphragm to include a perimeter comprising a diaphragm/housing interface which is configured to connect the dome shaped diaphragm with the ventricular housing to enclose a blood pumping chamber;

(ii) the diaphragm/housing interface to include an upward oriented, perimeter channel having a radius of curvature sufficient to prevent coagulation of blood within the channel during operation;

(iii) an intermediate annular section of the dome shaped diaphragm connected to the diaphragm/housing interface and perimeter channel in a configuration corresponding to that portion of the diaphragm when the ventricle is substantially at full systole; and c) removing the diaphragm from the mold.

Other objects features of the present invention will be apparent to those skilled in the art based on the following detailed description, taken in combination with the accompanying drawings.

DETAILED DESCRIPTION OF THE INVENTION

Figure 1:
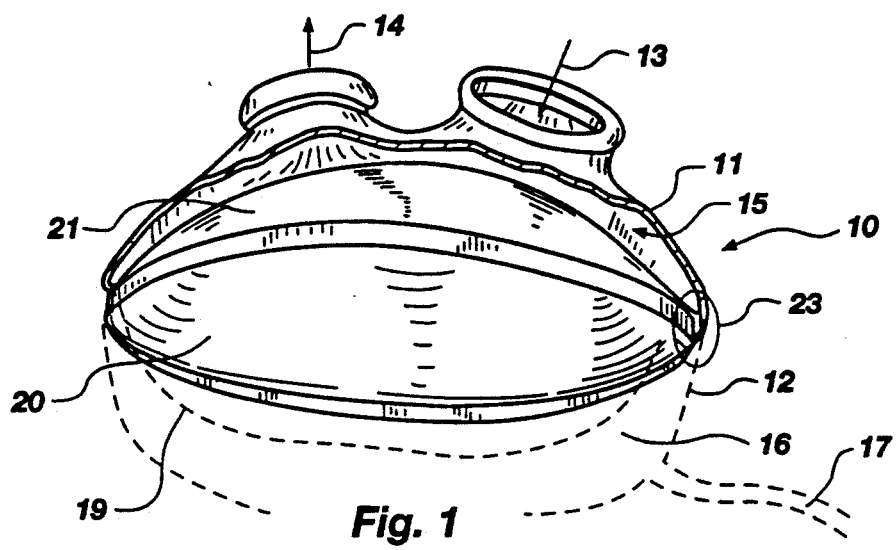
FIG. 1 shows a cut away, perspective view of the blood compartment of an artificial ventricle having a blood pumping membrane constructed in accordance with the present invention.

FIG. 1 shows an artificial ventricle 10 which may be used as a ventricle assist device or as part of the total artificial heart. The ventricle includes a ventricular housing 11, which represents the blood chamber portion of the ventricle (the pumping portion of the ventricle being represented by a base section 12 which is shown in phantom line). Inlet 13 and outlet 14 ports are positioned in a conventional manner within the ventricular housing 11 to provide unidirectional flow for blood into the blood pumping chamber 15. The pumping chamber 16 is enclosed within the base section or pumping housing 12 in a conventional manner and includes a drive line 17 which can be attached to a pneumatic source for pumping fluid. The attachment and operation of the pumping housing 12 is in accordance with conventional techniques and is not further developed in this description.

The pumping chamber 16 supplies the pumping fluid to sequentially displace a pumping diaphragm 20 between an extended position as illustrated in FIG. 1 (representing the ventricle at systole configuration) and a retracted position (not shown) wherein the pumping diaphragm 20 is pulled downward and extends toward the base of the pumping chamber as shown by phantom line 19 (representing the configuration of the ventricle in diastole).

The illustrated ventricle 10 includes a blood contacting membrane 21 which is formed as part of the pumping membrane 20. As will be shown hereafter, this membrane may be formed by a single process of injection molding, wherein the pumping membrane 20 is formed as a single structure with a blood contacting surface 21 which forms a portion of the blood chamber 15. This blood contacting membrane 21 may also be formed by other molding techniques, such as dip molding, solution casting, vacuum forming, pressure forming and similar techniques in which the desired dome structure may be mass produced.

A significant aspect of this blood contacting membrane arises in that the natural configuration of this membrane is substantially corresponding to the configuration of the membrane when in systole, in the absence of any pumping force. Typically, this is accomplished by molding the blood contacting membrane 21 (and associated pumping membrane 20) in the systole configuration wherein the dome structure extends upward. Because the polymer structure is molded in this configuration, elastic memory tends to bias the membrane in this natural position such that in the absence of any pumping force or resistance, the membrane would naturally return to its extended, dome shaped configuration. This is in contrast to typical pumping diaphragm configurations wherein the diaphragm membrane is molded in a position corresponding to diastole. In this position, the diaphragm is biased to a concave position wherein the pumping membrane extends into the pumping chamber 16.

Forming the membrane in the systole configuration offers numerous advantages. One of the most important of these advantages is that the diaphragm experiences virtually no loading stress at the diaphragm/housing junction 23. This is because the fully extended position wherein the diaphragm has forced blood from the chamber is actually the natural position to which the diaphragm is biased by reason of the fabrication of molding of the membrane in this original configuration. Although there may be internal stress, these are at equilibrium. Also, folding patterns with a tight radius of curvature which have occurred in prior art membrane structures tend to not occur with the diaphragm molded in the present, systole configuration. Typically, the systolic membrane will fold over a rigid base as shown at 19. The radius at periphery is quite large and introduces only minimal stress. This greatly contributes to improved survivability and reliability over extended periods of operation. Because of the lesser stress, a single layer pumping diaphragm is now feasible, providing new options for enhanced manufacturing techniques including injection molding.

Figure 2:
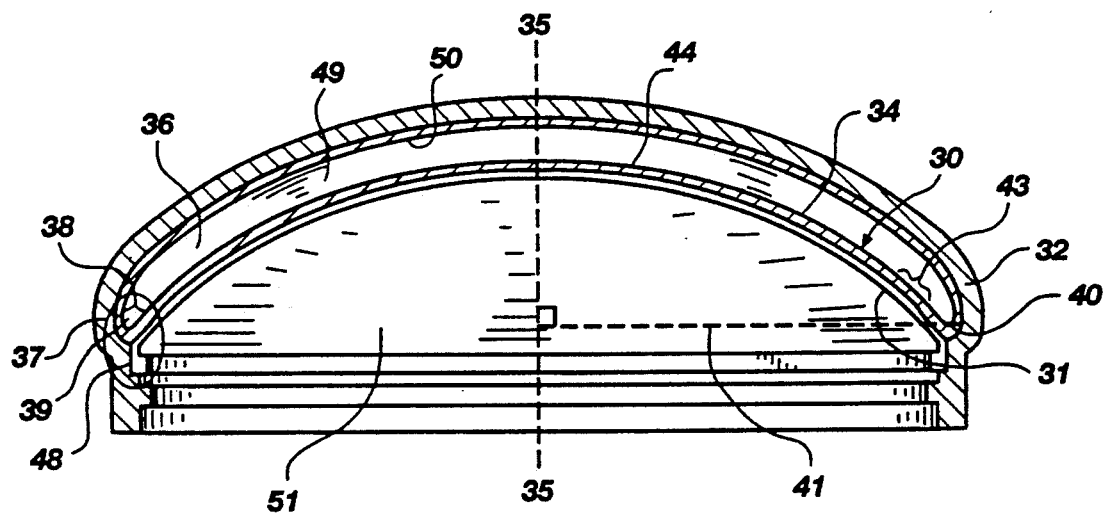
FIG. 2 shows a cross section of a ventricle similar to that illustrated in FIG. 1.

FIG. 2 illustrates in cross section more detailed construction representing dip molding or solution casting techniques. Specifically, this figure shows a flexible, blood contacting membrane 30 which includes a flexible, domed, polymer diaphragm 31 which is configured for placement within a ventricle housing 32 as part of a blood pumping structure. This diaphragm includes a blood contacting surface 34 which is formed on an upper face of the dome shaped diaphragm 31. As was previously indicated, this diaphragm is unstressed when in its natural, molded configuration which substantially corresponds to the systole condition within the ventricle. Geometrically, this occurs with the diaphragm 31 extending upward with respect to a vertical axis 35, which configuration forces blood from the blood chamber 36. The diaphragm 31 includes a diaphragm/housing interface 37 which forms a continuation 38 of the blood contacting surface 34. This diaphragm/housing interface includes a perimeter channel 39 which has a radius of curvature of sufficient size to prevent coagulation of blood flowing therein. This perimeter channel extends fully around the total perimeter of the diaphragm and is oriented upward relative to the vertical axis 35. Again, this configuration and orientation represents the unstressed condition of the subject diaphragm, corresponding to substantial full systole.

More particularly, the radius of curvature includes a low, concave arc section 40 which is oriented upward and includes a tangential component 41 which is substantially normal to the vertical axis 35. A locus of such tangential components formed around the vertical axis 35 forms a base reference plane which assists in defining further limitations with respect to the perimeter channel and diaphragm/housing interface.

Specifically, the referenced blood contacting surface extends from the point of origin 40 of the tangential component at the arc section inward to the juncture of the diaphragm/housing interface with the flexible, dome shaped diaphragm. Although there is not a clear definition of the exact location of this interface, reference numeral 43 suggests that there is a region slightly displaced from the radius of curvature in which the perimeter channel merges into the dome shaped configuration which provides the bulk of blood contacting surface. This blood contacting surface extending from (i) the point of origin of the tangential component to (ii) the general juncture of the diaphragm/housing interface with the flexible, dome shaped diaphragm provides a continuous, upward inclination with respect to the reference plane formed by tangential components 41, as measured around the full perimeter of the diaphragm.

Accordingly, when the subject blood contacting surface and/or dome shaped diaphragm is formed on a mold or injection molded, the diaphragm/housing interface is formed such that the perimeter channel 39 and the blood contacting surface 38 which forms a radius of curvature extending up to the juncture generally referenced as item 43 is naturally biased to this systolic configuration, at least around the perimeter. It is at this perimeter region that prior art devices have incurred substantial stress which has often led to failure of the diaphragm after numerous repetitions of pumping displacement. This stress free configuration in the systolic mode is important because of the added reliability and survivability of the diaphragm at this critical perimeter region.

In the preferred embodiment, the remaining upper section 44 of the diaphragm is also formed in this stress free, systolic configuration so that the total diaphragm is biased to the illustrated dome shape which corresponds to systole during ventricle operation. Because of the larger fold patterns within the upper region 44 of the diaphragm, a nonstressed condition within this area is not as critical. Therefore, some deformation may be acceptable during the molding or formation of this upper section 44.

Whereas prior art pumping diaphragms were generally multilayered, thin membranes, the present invention allows the use of a single layered diaphragm. Typically, this diaphragm or membrane will be less than 0.05 inches thick, but may be of other dimensions based on physical properties of the material which permit its flexing in a pumping mode without undue stress, particularly within the diaphragm/housing interface.

In the embodiment shown in FIG. 2, several stages of formation are represented. For example, the interior, dome shaped diaphragm 31 is a separate structure which is initially sealed to the ventricular housing 32 as is shown at junction 48. This junction between the ventricular housing and the diaphragm/housing interface is interbonded by appropriate adhesive to form an integral seal therebetween. The blood pumping chamber 49 is finally formed by providing a coating of blood compatible polymer which forms the continuous blood contacting surface 34, 38 and 50. This coating extends along the full interior surface of the blood pumping chamber 36 and actually forms the continuous blood contacting surface 38, along with the stated radius of curvature within the diaphragm/housing interface 37. As will be explained hereafter, this interior coating may be applied by solution casting techniques wherein liquid polymer is introduced through the ventricle openings 13 or 14, thereafter being disbursed across the interior surface to provide the continuous blood compatible surface structure. Best selection of appropriate materials is within the capacity of one skilled in the art. This coating generally becomes an integral part of a single diaphragm layer formed by the dome shaped diaphragm 31 and its coating 34. From this viewpoint, the solution coated diaphragm 30 physically becomes a single layer comprising a single pumping membrane interposed between the blood pumping chamber 36 and a pumping chamber 51 which receives the pumping fluid and related operational features of supporting pumping mechanism which is exterior to the blood pumping chamber 36.

Figure 3:
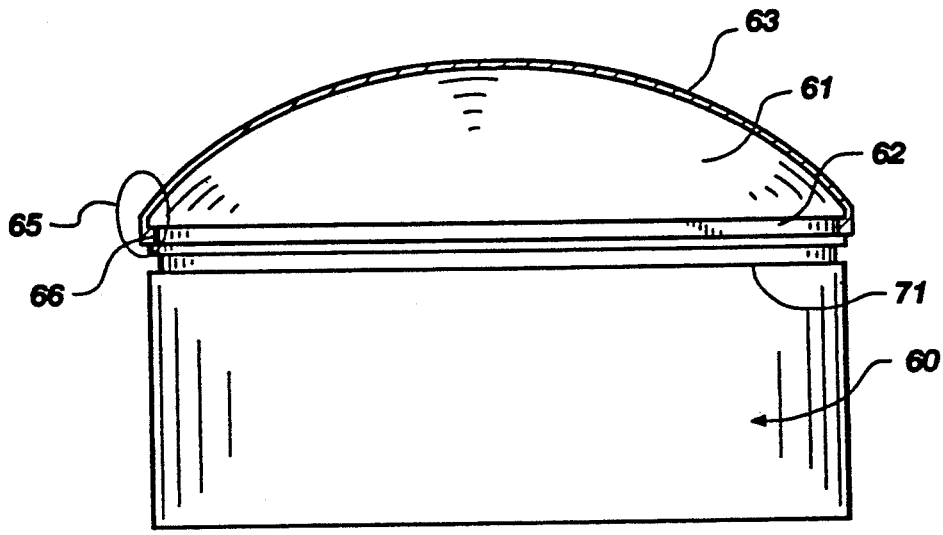
FIG. 3 depicts a mold with a pumping diaphragm constructed in accordance with the present invention shown in the cross section on the surface of the mold.

The foregoing structural features will become more clear in view of the following description of methodology for fabricating the flexible, blood pumping membrane configured and biased to the systolic position. For example, FIG. 3 discloses a mold 60 which includes a dome shaped surface 61 corresponding to the systole configuration to which the diaphragm is to be shaped. A first channel section 62 is formed within the upper mold portion 61 to provide for the formation of an extending rib which assists in coupling the blood pumping diaphragm 63 to a base housing which includes the pumping chamber. Accordingly, the first step in this methodology is to select a mold which is configured to provide the desired dome shaped diaphragm suitable for use within a ventricle housing as part of a blood pumping membrane as described above.

The next step is to form the dome shaped diaphragm 63 on the surface 61 of the mold. This step includes formation of a diaphragm housing interface 65 which forms a perimeter of the diaphragm and is configured to connect the dome shaped diaphragm with the ventricular housing by formation of rib element 66. It should be noted that this portion of the diaphragm structure 63 corresponds to the diaphragm illustrated in FIG. 2 as item 31. This structure is typically formed by dip molding techniques which are provided in detail hereafter.

The next step is to form a ventricular blood housing 70 and couple this housing at annular channel 71 on the mold 60. The junction 73 between the ventricular housing 70 and diaphragm 63 is then bonded to form an integral seal, such that the housing is closed except for at least one housing opening for permitting blood flow.

The next step involves forming a blood contacting surface 73 within the blood chamber 74 by coating the full interior surface 75 of the blood chamber with a blood compatible polymer. This forms a continuous blood contacting surface 72 which physically becomes a single layered diaphragm providing the benefits as previously described.

It will be apparent to those skilled in the art that the previous description of forming the dome shaped polymer 63 by dip molding, with the subsequent solution casting of liquid polymer to form the interior blood contacting surface 73 is only one means for accomplishing the inventive objective. For example, the dome shaped structure 63 may also be formed by blow molding, pressure forming and vacuum forming. As is disclosed hereafter, an injection molding technique can also be applied to develop the inventive structure.

Although the method of fabrication may vary, an important common feature of these various structures will be the presence of a diaphragm which substantially corresponds in its nonstressed configuration to the shape of the diaphragm when at systole in the ventricle. Similarly, one skilled in the art will note that the ribs 80 and 81 which have been formed in the diaphragm and ventricle housing and which provide means for tongue-in-groove attachment with a pumping base chamber may be substituted by other structure which accomplishes similar objectives. This illustrated tongue-in-groove structure is preferred in the present configuration because of its convenient structure for forming the integral attachment of the disclosed blood portion of the ventricle with the pumping chamber. These ribs are developed in the molding process by forming a perimeter rib 80 which extends inward from a lateral, internal face of the diaphragm/housing interface 76 which is below the dome shaped diaphragm. This rib 80 is sized to fit within a corresponding groove at an interior face of the pumping base chamber (not shown).

Figure 5:
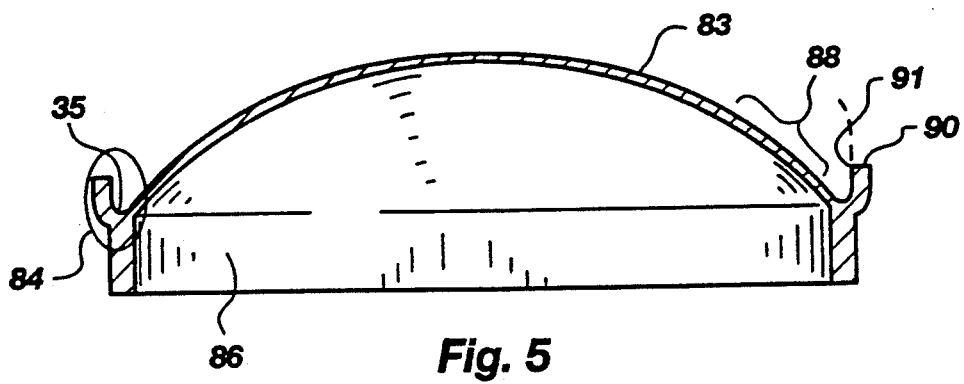
FIG. 5 shows a cross sectional perspective view of an additional embodiment of the subject pumping diaphragm which has been injection or injection/compression molded.

As is illustrated in FIG. 5, the present invention can be implemented by means of an injection molding process.

Such techniques have great advantages over the previously described molding techniques because of the adaptability of mass production and result in economic savings. Injection molding begins with the selection of a cavity mold which is appropriately formed to concurrently form (i) the dome shaped diaphragm 83 with blood contacting surface, (ii) the diaphragm/housing interface 84 and (iii) included perimeter channel 85 with the designated radius of curvature. Obviously, as an injection molded technique, this structure is formed concurrently with a single procedure. Also formed is the contacting structure 86 for attachment of the base pumping chamber.

In circumstances where the diameter of the dome shaped diaphragm 83 is 2 inches or less, a single step injection molding procedure can be accomplished because the thickness of the diaphragm is within the operational limitations of polymer flow within the mold cavity. The workability of a single injection molding procedure has been confirmed specifically with a dome shaped diaphragm having a 1.5 inch diameter. Lesser sizes of diaphragms would have even less difficulty in securing polymer flow within the cavity to develop a proper injection molded structure.

In instances where the dome structure has a diameter greater than 2 inches, the injection molding step may be followed by a compression molding procedure in which the final dome structure is configured. Specifically, this method involves selecting a mold which facilitates both the injection and compression molding process and which is initially configured to form an oversized dimension for the dome shaped diaphragm and its associated diaphragm/housing interface and perimeter channel. This over sized configuration is subsequently reduced by the compression aspect of the mold to form the final, smaller dimensions. Such procedures are known to those skilled in the art and need no further explanation. Such techniques may be necessary for diameters exceeding 1.5 inches and will probably be necessary in all cases where the diameter exceeds 2 inches. Typically, diaphragm thickness for the injection molding stage of this process will be at least approximately 0.1 inches, with the subsequent compression step reducing the diaphragm to a thickness of less than approximately 0.05 inches. A preferred thickness for the final diaphragm is 0.030 inches and is well within the capability of the compression molding procedure.

As with previous structures described, the present injection molded structure of FIG. 5 includes the reference dome shaped diaphragm 83 and a diaphragm/housing interface in which the perimeter channel 85 is oriented upward and includes the stated radius of curvature to prevent blood coagulation within the channel during ventricle operation. An intermediate annular section 88 which extends from the diaphragm/housing interface 84 includes a formed configuration which corresponds to that portion of the diaphragm when the ventricle is substantially a full systole.

In all of the respective molding techniques illustrated, the final step of procedure is to remove the diaphragm from the mold. This is followed by subsequent steps of attaching the diaphragm to ventricle structure as either a ventricle assist device or total artificial heart. The diaphragm illustrated in FIG. 5 can be coupled to a ventricle housing similar to that shown in FIG. 4 above the dashed lines 89. This upper ventricle housing can be sealed at the top face 90 of the injection molded structure and the remaining juncture 91 may be finally formed by radio frequency welding or other techniques to create a smooth, blood compatible surface.

These procedures are illustrated in the following two examples.

EXAMPLE 1

Dip Coating or Solution Casting of Single Layer Diaphragm

A ventricular housing was fabricated using the following procedure:

1. 500 grams of TECOFLEX (TM) 60-D SG a medical grade polyether polyurethane was dissolved in 1800 milliliters of dimethylacetimide and was stirred to a consistent viscosity.
2. Inflow and outflow port dummy rings were screwed onto the ventricular housing molds for right and left ventricles. The molds and rings were then cleaned with ethanol.
3. The mold was primed with DMAC and was dipped three times in 20 percent BIOLON (TM) a medical grade polyether polyurethane or was similarly poured with the same material. After each dipping or pouring, the coating was cured for one hour at 45 degrees centigrade in a convection oven. Subsequent layers were followed by similar curing stages. The mold was then dipped 16 times with TECOFLEX (TM) 60-D SG, curing in the same manner. Finally, the structure is cured for at least two days, annealed, and then removed from the mold.

A systolic diaphragm was fabricated as follows:

1. A clean mold was selected such as the configuration shown in FIG. 3.
2. Groove 62 was then primed with DMAC.

3. Using BIOLON (TM) twenty percent solution, the mold was dipped five times, curing in between each dip for one and one-half hours.

4. The molded structure was then cured overnight and the bottom groove was removed in groove 71.

Figure 4:
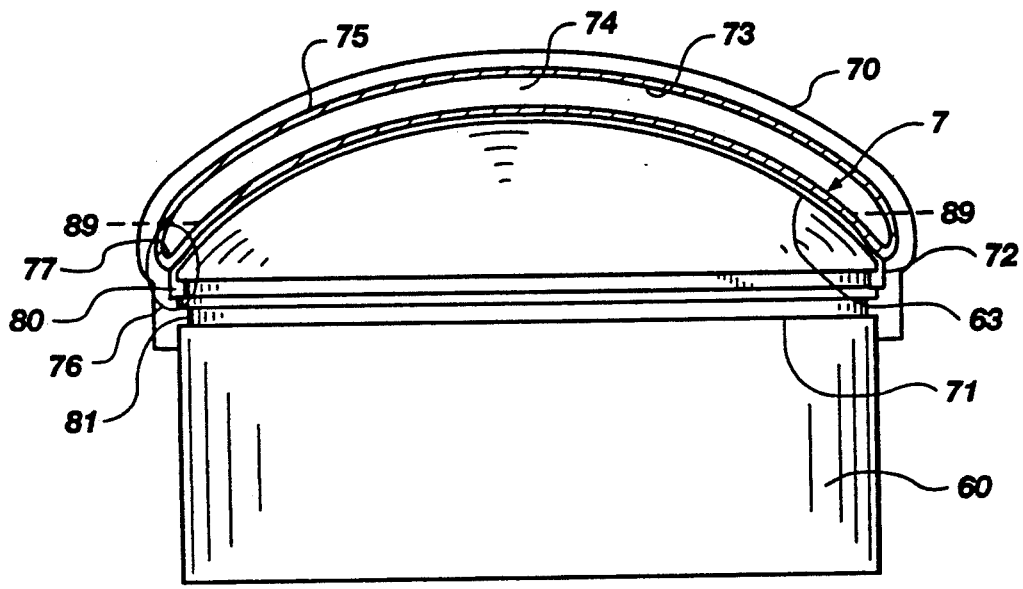
FIG. 4 shows a mold with a ventricular housing which encloses the blood chamber in combination with the pumping diaphragm illustrated in cross sectional view.

A blood contacting surface as illustrated in FIG. 4 was prepared as follows:

1. The ventricular housing 70 was placed over the diaphragm 63, matching grooves and hash marks for proper orientation.

2. A ten percent BIOLON (TM) solution was heated to a temperature of 70 degrees centigrade.

3. The interface 72 between the diaphragm and housing was glued, using a portion of the 20 percent BIOLON.

4. The heated ten percent BIOLON (TM) solution was poured into the cavity through the inflow and outflow ports. Excess BIOLON (TM) was then poured from the cavity and the remainder of the polymer was allowed to settle into the diameter/housing interface to form the perimeter channel 77 with the desired radius of curvature. Care was taken to ensure that the distribution was even around the perimeter of this diameter/housing interface. The molded product was allowed to cure for two days at 45 degrees centigrade in a convection oven.

5. The molded product was then annealed and removed from the mold.

EXAMPLE 2

A procedure for injection molding a blood pumping membrane in systole configuration is as follows:

1. A injection mold cavity is secured by providing design parameters, dimensions, tolerances and other relevant information for manufacture of the mold.

2. The various components providing the injection molded cavity are assembled, including the valves, housings, diaphragm and connections, etc., to form a completed ventricle cavity.

3. For diameters which are less than 1.5 inches, the single stage injection molding device will provide an acceptable diaphragm. This is accomplished by applying conventional injection molding techniques utilizing a suitable material such as PELLETHANE (TM) 80A a medical grade polyether polyurethane and TICOFLEX (TM) 80A. Other materials which provide compatible blood contacting surfaces may also be used. In all instances, the material must be capable of flexing at least 150 million cycles without failure.

Injection molding a larger diameters than 1.5 or 2 inches may be accomplished in combination with a compression molding system. In this case, the diaphragm is first injection molded into a thicker cross section of approximately 0.15 inches in thickness. The structure is then compressed to a final thickness of approximately 0.030 inches utilizing combined injection/compression molding equipment which substantially performs both functions at the same time.

4. The finished components are removed from the mold and are finished processed in accordance with known techniques.

Although specific examples have been provided for the diaphragm structure and method of fabrication, it will be understood by those skilled in the art that these examples are merely exemplary. Accordingly, the invention is to be construed in accordance with the following claims and not with respect to specific examples provided herein.

We claim:

1. A method for fabricating a flexible, blood pumping membrane for use within a ventricle, comprising the steps of:
   a) selecting a mold having a convex mold surface and being configured to provide a dome shaped diaphragm suitable for use within a ventricular housing as a part of a blood pumping membrane;
   b) forming on the convex surface of the mold the dome shaped diaphragm to include
      (i) a perimeter comprising at least a portion of a diaphragm/housing interface which is configured to connect the dome shaped diaphragm with the ventricular housing to enclose a blood pumping chamber;
      (ii) an intermediate annular section of the dome shaped diaphragm extending inward from the diaphragm/housing interface in a configuration corresponding to that portion of the diaphragm when the ventricle is substantially at full systole, such that elastic memory of the molecular structure of said annular section acts to bias the membrane toward a natural, end-systolic position to thereby minimize physical stress of the annular section during pumping of the membrane; and
   c) removing the diaphragm from the mold.

2. A method as defined in claim 1, wherein the dome shaped diaphragm and the portion of the diaphragm/housing interface are formed as a single layer of polymer material which operates as a single pumping diaphragm between a blood chamber and pumping chamber of the ventricle.

3. A method as defined in claim 1, wherein the dome shaped diaphragm is prepared by dip molding.

4. A method as defined in claim 1, wherein said mold has a dome shaped configuration which substantially corresponds to the shape of a pumping diaphragm at systole.

5. A method for fabricating an artificial ventricle and forming a flexible, blood pumping membrane within said ventricle comprising the steps of:
   a) selecting a mold having a convex mold surface and being configured to provide a dome shaped diaphragm suitable for use within a ventricular housing as a part of a blood pumping membrane;
   b) forming on the convex surface of the mold the dome shaped diaphragm to include
      (i) a perimeter comprising at least a portion of a diaphragm/housing interface which is configured to connect the dome shaped diaphragm with the ventricular housing to enclose a blood pumping chamber;
      (ii) an intermediate annular section of the dome shaped diaphragm extending inward from the diaphragm/housing interface in a configuration corresponding to that portion of the diaphragm when the ventricle is substantially at full systole, such that elastic memory of the molecular structure of said annular section acts to bias the membrane toward a natural, end-systolic position to thereby minimize physical stress of the annular section during pumping of the membrane;
   c) removing the diaphragm from the mold;
   d) affixing a ventricular blood housing around the dome shaped diaphragm by forming a junction between the ventricular housing and the portion of the diaphragm/housing interface forming part of the diaphragm, said junction being interbonded to form an integral seal therebetween, said housing including at least one opening for blood flow; and e) coating the full interior surface of the blood chamber with a blood compatible polymer to form a continuous blood contacting surface including an upward oriented, perimeter channel having a radius of curvature sufficient to prevent coagulation of blood within the channel during operation.

6. A method as defined in claim 5, wherein the step of coating the blood chamber with polymer comprises introducing liquid polymer having blood compatibility through the at least one opening and dispersing the liquid over the interior surface to provide a smooth blood contacting surface which is continuous from the at least one opening across the interior surface of the ventricular blood housing, diaphragm/housing interface and dome shaped diaphragm.

7. A method as defined in claim 6, wherein the liquid polymer within the blood chamber is formed into the blood contacting surface by solution casting the liquid polymer over the surface of the dome shaped diaphragm to form a single pumping membrane which separates a blood chamber from a pumping chamber which contains pumping fluid for sequentially driving the membrane from systolic to diastolic configurations, said membrane being biased to the systolic configuration in which it was originally formed.

8. A method as defined in claim 5, wherein the step of forming the diaphragm/housing interface includes forming (i) a perimeter rib extending inward from a lateral, internal face of the diaphragm/housing interface below the dome shaped diaphragm to provide for attachment of a pumping base chamber with a corresponding groove at an exterior face for tongue-in-groove attachment.

9. A method as defined in claim 8, wherein the step of forming the diaphragm/housing interface includes forming (i) a perimeter rib extending inward from a lateral, internal face of the diaphragm/housing interface below the dome shaped diaphragm to provide for attachment of a pumping base chamber with a corresponding groove at an exterior face for tongue-in-groove attachment.

* * * * *

UNITED STATES PATENT AND TRADEMARK OFFICE
CERTIFICATE OF CORRECTION

PATENT NO. : 5,324,464
DATED : June 28, 1994
INVENTOR(S) : Holfert et al.

It is certified that error appears in the above-indentified patent and that said Letters Patent is hereby corrected as shown below:

On the title page, Item [54], Column 1, the title should read:

"Method of Making a Blood Pumping Membrane for Artificial Ventricles"

Signed and Sealed this

Twenty-ninth Day of November, 1994

Attest:

BRUCE LEHMAN

Attesting Officer

Commissioner of Patents and Trademarks